United States Patent [19]

Dowdle

[11] Patent Number: 4,902,623
[45] Date of Patent: Feb. 20, 1990

[54] PLASMINOGEN ACTIVATOR

[75] Inventor: Eugene B. D. Dowdle, Cape Town, South Africa

[73] Assignee: South African Inventions Development Corporation, Pretoria, South Africa

[21] Appl. No.: 915,599

[22] Filed: Oct. 3, 1986

Related U.S. Application Data

[63] Continuation-in-part of Ser. No. 843,405, Mar. 24, 1986, which is a continuation of Ser. No. 559,569, Dec. 8, 1983, abandoned, which is a continuation-in-part of Ser. No. 513,145, Jul. 12, 1983.

[30] Foreign Application Priority Data

Dec. 14, 1982 [ZA] South Africa ................. 82/9168
Jan. 11, 1983 [AU] Australia ..................... 10296/83

[51] Int. Cl.$^4$ .................. C12N 9/24; A01N 65/00; A61K 35/78
[52] U.S. Cl. ......................... 435/226; 435/814; 435/815; 424/195.1
[58] Field of Search .............. 435/13, 23, 24, 174, 435/184, 212, 214, 215, 216, 217, 226, 814, 815; 424/94, 101, 195.1

[56] References Cited

U.S. PATENT DOCUMENTS 4,165,258  8/1979  Pye et al. ..................... 435/215
4,245,051  1/1981  Reich et al. .................. 435/212

OTHER PUBLICATIONS

Heussen et al., *Haemostassis*, 11 (Suppl. 1):47 (1982).
Rijken et al., *J. Biol. Chem.*, 257(6):2920–2925 (Mar. 25, 1982).
Heussen et al., *J. Biol. Chem.*, 259(19):11,635–11,638 (Oct. 10, 1984).

*Primary Examiner*—Elizabeth C. Weimar
*Attorney, Agent, or Firm*—Millen, White & Zelano

[57] ABSTRACT

For selectively and reversibly adsorbing tPA, pro-tPA or mixtures thereof, from an aqueous medium, for example, derived from a melanoma cell culture, the aqueous medium is intimately contacted with an affinity reagent comprising an immobilized Kunitz-type inhibitor, substantially as occurs in and is extractable from seeds of an Erythrina species, e.g., *Erythrina latissima*, having Erythrina species, the following combination of characteristics:

(a) it is an inhibitor of the Kunitz-type;
(b) it inhibits trypsin;
(c) it inhibits plasmin;
(d) it has no effect on urokinase;
(e) it inhibits tPA; and
(f) in its immobilized form, it is a selected adsorbent for tPA and its precursor pro-tPA, to thereby cause the tPA, pro-tPA or mixtures thereof to become selectively adsorbed on the affinity reagent.

14 Claims, No Drawings

PLASMINOGEN ACTIVATOR

CROSS-REFERENCE TO RELATED APPLICATIONS

This application is a continuation-in-part of abandoned application Ser. No. 843,405, filed Mar. 24, 1986, which is a continuation of abandoned application Ser. No. 559,569, filed Dec. 8, 1983, which in turn is a continuation-in-part of abandoned application Ser. No. 513,145, filed July 12, 1983.

INTRODUCTION

The present invention relates to an inhibitor for tPA, an affinity reagent comprising the inhibitor and a process for selectively and reversibly adsorbing tissue plasminogen activator (tPA) and/or its precursor (pro-tPA) from aqueous media containing it, in particular for preparing or isolating plasminogen activators, namely tPA and/or its precursor pro-tPA.

The affinity reagent has the unique property of selectivity for tPA and pro-tPA to the exclusion of other plasminogen activators even urokinase which in some tissues occurs side by side with tPA.

Recombinant DNA technology has recently made available mutagenic variants of tPA and pro-tPA which differ from the natural proteins by replacement, removal or addition of one or more amino acid residues. The terms "tPA" and "pro-tPA" as used herein include such variants provided they retain the site or sites having an affinity for the reagent of the invention.

BACKGROUND OF THE INVENTION

The utility of the invention will be apparent from the following:

Plasminogen activators are enzymes which by their action upon plasminogen (a precursor of plasmin) result in the formation of plasmin. Plasmin in turn acts upon fibrin (or blood clots) to liquefy or dissolve the fibrin. Plasmin also causes lysis of fibrinogen which is a precursor of fibrin.

The foregoing effects play an important role in the natural fibrinolytic systems. They are also put to use in the therapeutic administration of plasminogen activators for the management, treatment or prophylaxis of thrombotic disease or other conditions where it is desirable to produce local fibrinolytic or proteolytic activity via the mechanism of plasminogen activation.

They may also find use in reagents for diagnostic, pathological or scientific tests involving fibrinolysis in vitro.

Two activators of human plasminogen are extensively used. The first of these is the bacterial enzyme streptokinase, which functions by a non-proteolytic mechanism. The second is the protease urokinase, which is mainly obtained from urine or cultured kidney cells and also by recombinant DNA procedures. These two compounds have the therapeutic disadvantage that their action is not confined to plasminogen associated with fibrin in blood clots. They act upon plasminogen generally in the circulation and, in consequence, produce widespread plasmin generation with extensive lysis of fibrinogen, the precursor of fibrin. This may in turn lead to a bleeding state as a result of ineffective normal coagulation of the blood. Streptokinase, being a foreign antigen, elicits an immune response in the patient. The resulting antibodies neutralize the action of streptokinase on plasminogen and hence diminish its therapeutic efficacy.

Much attention has therefore recently been given to a third plasminogen activator, referred to generally as "tissue plasminogen activator" hereinafter referred to as "tPA". This enzyme is found in most human tissues and is identical to or indistinguishable from an enzyme that it also a characteristic secretory product of human melanoma cells cultured in vitro. Although it catalyzes the proteolytic activation of plasminogen in much the same way as does urokinase, tPA differs from urokinase in a number of important respects. The two enzymes are chemically dissimilar. They have different molecular weights and each fails to react with antibodies to the other enzyme. The catalytic action of tPA is enhanced by fibrin, whereas that of urokinase is not. tPA has the important property that it binds to fibrin, whereas urokinase fails to do so. These facts were recorded in a recent article entitled "Purification and characterisation of the plasminogen activator secreted by human melanoma cells in culture" by Dingeman C. Rijken et al. (J. of Biological Chem., 256, (13); 7035–7041). That same article also describes the preparation of tPA from a cultured human melanoma cell line as well as from normal human tissue. The purification procedure consisted of successive chromatography on zinc chelate-agarose, concanavalin A-agarose and sephadex G-150 in the presence of detergent.

The tendency for tPA to bind to fibrin, its greatly enhanced fibrinolytic action in the presence of fibrin and, when compared to urokinase and streptokinase, its relatively inefficient function as a plasminogen activator in the absence of fibrin, combine to make tPA a plasminogen activator of choice for human thrombolytic therapy. Interactions between fibrin and tPA to a considerable extent localize the plasmin generation to the site of the clot and mitigate or avoid the consequences of promiscuous plasminogen activation as observed when urokinase or streptokinase is used. Furthermore, tPA is a protein which is immunochemically compatible with man, whereas streptokinase is not, being a foreign protein.

Recent reports, e.g., "Specific lysis of an iliofemoral thrombosis by administration of extrinsic (tissue type) plasminogen activator" by W. Weimar et al. (Lancet, November 7, 1981, page 1018), F. van der Werf et al. (New England J. of Med., (10); 609–613 (1984)) and the SPECIAL REPORT on the "Thrombolysis in Myocardial Infarction Trial" published in New England J. of Medicine, 312, (14); 932–936 (1985), testify to the clinical usefulness of tPA in the treatment of human thrombotic diseases.

According to P. Wallen et al, (Prog. Chem. Fibrinolysis Thrombolysis 5, 16–23 (1981)) tPA, occurs in two different forms, one being a single-chain form which is converted by plasmin or trypsin into two chains linked by disulphide bridges, and which those authors consider to be a degradation product of the former.

There are reasons why the single-chain form is rather to be considered the precursor of tPA. It will therefore be referred to herein as pro-tPA.

It has been found that the two molecular forms of tPA, in the presence of fibrin, exhibit very similar lysis times, because once the pro-tPA has been converted into tPA, it acts on the clot in the same manner as if it had been adsorbed in the form of tPA in the first instance. This observation is also in accordance with the work of other researches, e.g., Dingeman, Rijken, Hoylaerts and Collen (J.Biol.Chem., 257, 2920–2925

(1982), European patent application No. 0041 766).

The conversion of pro-tPA into tPA can be inhibited if desired (even in the presence of enzymes which would normally catalyze such conversion) by aprotinin, which is a protease inhibitor.

The therapeutic value of tPA as well as of pro-tPA is now generally accepted. However, until recently no method was known which would lend itself readily to the purification of two-chain tPA on a commercial scale, nor of the single chain form herein referred to as "pro-tPA".

Human tPA is present in tissue extracts, vessel perfusates and mammalian cell cultures. More recently, attention has been given to secure the expression of tPA by recombinant DNA technology in certain mammalian host cells, yeasts and bacteria. In all cases, the tPA enzyme is present in very low concentrations, usually of the order of a few milligrams per liter of culture fluid. Thus, to produce tPA efficiently on a commercial scale, a method is required to easily extract the tPA enzyme occurring in small quantities in a complex mixture of interfering proteins, cell debris and the like which are present in the cell culture medium. Moreover, such a method must achieve a high recovery of tPA from the harvest fluid and produce a product of high purity if the enzyme is to be administered intravenously. Also, a method must permit a high rate of production if it is to be used on a commercial scale.

A method proposed by Dingeman et al. (J.Biol. Chem., 256, (13), 7035–7041) uses a cumbersome three-step procedure giving a low rate of production because it incorporates a size exclusion chromatographic step. While this method produces a high degree of purification, the quoted recovery of tPA is relatively low.

The method employed by Wallen et al. referred to above (loc.cit,) produces slightly higher yields but much poorer purification. (Eur. J.Biochem., 132, 681–686 (1983).

Nielsen et al. (The EMBO J., 2, (1), 115-119) use immobilized monoclonal antibodies to tPA in a single step affinity purification. By that method improved yields and a reasonable purification are attained, compared with the above. However, the long term stability of monoclonal antibodies after repeated use for the immuno purification of tPA leaves much to be desired in that there is a danger of leakage of foreign proteins into the final tPA preparation.

SUMMARY OF THE INVENTION

It is an object of the present invention to provide a new and relatively simple process for the manufacture of tPA.

It is a further object to provide a process as aforesaid, suitable for manufacturing a precursor of tPA, hereinafter referred to as "pro-tPA", which has therapeutic properties. It is a further object to provide processes as aforesaid, capable of separating tPA and pro-tPA from urokinase and which if desired, can be adapted to the separate recovery of urokinase.

It is yet a further object to provide a novel affinity reagent suitable for the above process and for the selective adsorption of tPA and/or pro-tPA.

Having regard to the aforegoing, the present invention, according to one aspect thereof, provides a process for selectively and reversibly adsorbing tPA, pro-tPA and mixtures of both, as the case may be, from an aqueous medium containing such substance or substances in solution which comprises intimately contacting the aqueous medium with an affinity reagent comprising an immobilized Kunitz-type inhibitor, substantially as occurs in and is extractable from seeds of Erythrina latissima and other Erythrina species and which is distinguished from other inhibitors occurring in such species by the following combination of characteristics:

(a) it is an inhibitor of the Kunitz type;
(b) it inhibits trypsin;
(c) it inhibits plasmin;
(d) it has no effect on urokinase;
(e) it inhibits tPA; and
(f) in its immobilized form, it is a selective adsorbent for tPA and its precursor pro-tPA, to thereby cause selectively the tPA, pro-tPA or mixture of both to become adsorbed on the affinity reagent.

The inhibitor is thus an inhibitor of a variety of enzymes, i.e., it has sites capable of inhibiting these enzymes. The inhibitor also has no effect on thrombin.

The aforesaid combination of properties according to present knowledge is a unique combination.

The seed of Erythrina latissima (broad-leafed Erythrina) and other Erythrina species have recently been found to contain several proteinase inhibitors (Francois J. Joubert et al., Z. Physiol.Chem., 362 531–538 (1981)). In the particular case of E. latissima, two chromatography fractions being the first and thrid eluates from a DEAE sepharose column and referred to in that publication as DE-1 and DE-3 respectively showed enzyme inhibition activity. These are arbitrary code numbers for two of several protein fractions isolated chromatographically from E. latissima. As disclosed in that publication, whereas fraction DE-1 inhibits bovine chymotrypsin and not bovine trypsin, fraction DE-3 inhibits trypsin but not chymotrypsin.

Those findings had been of scientific interest but not of any industrial and commercial utility.

After screening hundreds of enzyme inhibitors, it has now been discovered by the inventor that this protein fraction, code-named DE-3, isolated chromatographically from the seeds of E. latissima and from the seeds of other Erythrina species, has the unique property of being also an inhibitor of tPA and being even capable of distinguishing between tPA and urokinase.

It has furthermore now been found that if this inhibitor is immobilized, e.g., in manners known per se, it forms an affinity reagent which selectively extracts by adsorption tPA and pro-tPA, while leaving the contaminants unadsorbed in the aqueous solution.

These properties can therefore be utilized for the concentration and purification of tPA and pro-tPA not only for scientific but, more importantly, for the large-scale commercial preparation of tPA and/or pro-tPA from transformed cells or from natural sources.

Thus, the present invention, for the first time, provides the basis which justifies the manufacture of the substance as a new commercial product in commercially useful quantities for use as an inhibitor for tPA and pro-tPA, useful for the preparation of a new affinity reagent to be used in a process for the purification of tPA and/or pro-tPA.

The kind of protein fraction, which in the case of E. latissima has been code-named DE-3, has been found to occur in the seeds of all of the numerous Erythrina species tested to date. The other Erythrina species are E. lysistemon, E. caffra, E. acanthrocarpa, E. zeyheri, E. decora, E. corallodendron, and E. humeana. The kind of protein fraction is therefore considered to be common to substantially all Erythrina species.

Surprisingly, it is a peculiarity of the affinity reagent that other plasminogen activators, e.g., urokinase, if present in an aqueous solution, are not adsorbed. Accordingly, the affinity reagent can be used as a selective adsorbent for tPA and pro-tPA even if the tPA and/or pro-tPA is contaminated with urokinase, as the urokinase is removed with the non-adsorbed contaminants. This means that the process can be applied to recover selectively tPA and/or pro-tPA from a large number of sources such as various kinds of body fluids or tissue or cell cultures wherein tPA and/or pro-tPA occur, even if in mixture with urokinase.

The affinity reagent can of course also be used for analytical purposes, e.g., for distinguishing between tPA or pro-tPA and other plasminogen activators, e.g., urokinase.

One suitable aqueous liquid to be used for the extraction of tPA and/or pro-tPA therefrom is a harvest fluid, preferably serumfree, obtained from a tissue culture of human melanoma cells containing tPA and/or pro-tPA in the secretory products of the cells.

In accordance with preferred embodiments, the tPA and/or pro-tPA is adsorbed by passing the aqueous medium containing it through a bed of the affinity reagent, followed by washing the bed and subsequent desorption of the tPA and/or pro-tPA and washing the desorbed tPA and/or pro-tPA off the bed. The bed may for example be in the form of a column.

The desorption may be carried out with aqueous potassium thiocyanate solution preferably from about 1 to 3 molar, e.g., from 1.4 to 2 molar, preferably 1.6 molar at a pH at which tPA is stable, preferably dissolved in approximately neutral phosphate buffered saline, e.g., between 0.3 and 1 molar, preferably about 0.4 molar in respect of NaCl and preferably containing a stabilizing amount of a suitable surfactant, e.g., 0.1% Triton X-100 or Tween. The desorption may be carried out with chaotropic desorbents other than potassium thiocyanate. The desorption may also be carried out at low pH, e.g., from 2 to 3.5, preferably from 2.8 to 3. Other suitable desorbing conditions are high salt concentrations and/or the presence of arginine and/or the presence of benzamidine. Such desorbing conditions are known to persons skilled in the art and therefore require no detailed description.

Also according to the invention, if it is desired to recover tPA free of pro-tPA, any pro-tPA, whether produced by the process steps described further above or not, may be readily converted enzymatically into tPA, e.g., by exposing the pro-tPA in aqueous solution to the action of plasmin or enzymes having an equivalent effect on pro-tPA. Such an enzyme, as yet unidentified, occurs for example in fibrin for which reason the conversion of pro-tPA into tPA also occurs in the presence of fibrin. Kallikrein also produces this effect, albeit less effectively.

On the other hand, according to a further important aspect of the invention, it has been found that, e.g., for therapeutic purposes, pro-tPA can be used directly and has properties which are considered desirable. With tPA, there still exists a limited possibility that it may activate some plasminogen in the bloodstream rather than at the fibrin site where the localized action is desired. Pro-tPA, which has only very weak plasminogen activating properties, acts selectively in that it first attaches itself to fibrin and is only then converted into tPA at the fibrin site. This tPA in turn releases plasmin right at the fibrin site which in turn acts to dissolve the clot. This means that the effect of pro-tPA tends to be confined to the desired site of action.

Pro-tPA differs from tPA in that the former is a single chain compound which has only weak plasminogen activator properties, whereas tPA (molecular weight 72 000 dalton) is a double chain compound and has pronounced plasminogen activator properties. Pro-tPA has the same molecular weight as tPA.

The present invention also provides a process for the recovery of pro-tPA from an aqueous medium containing it and also containing plasmin and/or plasminogen and a plasminogen activator which comprises inhibiting plasmin in the aqueous medium and removing the pro-tPA from the aqueous medium while plasmin is inhibited. In this context it is pointed out that tPA, when present, acts as a plasminogen activator causing plasmin to be formed, which in turn must be inhibited.

The pro-tPA is adsorbed from the aqueous medium by an affinity reagent in accordance with the invention which is an inhibitor for plasmin which also has an affinity for pro-tPA and is subsequently desorbed and recovered in purified form. The pro-tPA thus recovered may then be sterilized and stabilized with a physiologically compatible stabilizer in the form of an intravenously injectable aqueous solution.

As regards potential sources of tPA or pro-tPA, human tissue plasminogen activator is present in blood, tissue extracts, vessel perfusates and cell cultures but in extremely low concentrations. An alternative source of tPA is listed in EPO Application No. 812 00643-5, which describes a melanoma cell culture capable of producing tPA in higher concentrates than generally found in the foregoing sources.

More recently, increasing attention has been given to the application of recombinant DNA techniques for the expression of tPA in relatively high concentration, mainly in mammalian cell lines, e.g., Chinese hamster ovary cells, fibroblasts, yeasts and bacteria. By such recombinant DNA technology, the human gene encoding for tPA is transvected into the host cell which is thereby transformed to synthesize the tPA enzyme. By the method of gene amplification, an increase in the concentration of tPA is obtained. These procedures are described in SA Patent Application No. 83/3174, EPO Publication Nos. 117 059 and 117 060. As indicated above, such techniques are capable of providing mutagenic variants of tPA and pro-tPA.

Whereas the earlier specific disclosures were largely confined to "natural" tPA and pro-tPA in particular when recovered from Bowes melanoma cell cultures, it should be stressed that the process can be practiced successfully in an analogous manner with tPA and pro-tPA from all possible sources including substances which have been produced by genetic engineering techniques e.g., expressed in E. coli or other bacteria, Yeasts, Chinese hamster ovary cells and other mammalian cells.

The latter produce a glycosilated form of tPA or pro-tPA which is said to be indistinguishable from the "natural" substance. But genetically engineered tPA, expressed in E.coli, produces a non-glycosilated form of tPA which can also be adsorbed and purified according to the present invention as effectively as the natural product. The tPA produced by yeasts is glycosilated but not identical to the tPA produced by mammalian cells.

According to a further aspect of the present invention, it is possible to recover tPA and/or pro-tPA separately and in addition to urokinase from aqueous media containing both plasminogen activators (as such or as a precursor). This can be done by contacting such an aqueous medium with an affinity reagent as defined above, thereby selectively adsorbing the tPA and/or pro-tPA from the solution, removing the affinity reagent loaded with tPA and/or pro-tPA from contact with the aqueous medium depleted of tPA and/or pro-tPA, but still containing the urokinase, and recovering urokinase from the aqueous medium depleted of tPA and/or pro-tPA. Suitable aqueous media for this process will be aqueous extracts of random mammalian tissue cells or media containing the secretion products of such cells, since such media contain both plasminogen activators. Once again, the adsorbed tPA and/or pro-tPA may be desorbed and recovered, and if, desired, pro-tPA may be converted into tPA either before or after the adsorption on the selective affinity reagent.

The urokinase may be recovered from the aqueous medium in any suitable manner, for example, by being adsorbed from the aqueous medium using an affinity reagent having an affinity for urokinase. Such affinity reagents may be immobilized inhibitors having no selectivity for tPA over urokinase. It is also possible to use as an affinity reagent antibodies against urokinase, suitably immobilized in a manner known per se.

Also in accordance with the invention, there is provided a new affinity reagent which comprises an enzyme inhibitor comprising the following combination of characteristics:

(a) it is of a type occurring in the seeds of Erythrina species (e.g., in a fraction code-named DE-3 from *E. latissima* and similar fractions in other species);
(b) it is an inhibitor of the Kunitz type;
(c) it inhibits trypsin;
(d) it inhibits plasmin;
(e) in contrast to other inhibitors occurring in Erythrina seed, it inhibits tPA yet has no effect on urokinase; and
(f) in its immobilized form, it is a selective biosorbent for tPA and its precursor pro-tPA, immobilized by being bonded to a solid carrier, e.g., by being covalently bonded to the carrier.

For example, the inhibitor may be coupled to cyanogen bromide-activated agarose in a manner known as such to persons skilled in the art. However, other solid carriers and coupling agents can be used depending on the chemical properties of the surface to which the inhibitor is to be coupled. Examples are:

(a) carbodiimide coupling which couples free amino groups to free carboxy groups;
(b) glutaraldehyde coupling which couples NH$_2$ groups to agarose previously converted into the aminoalkyl form;
(c) periodate activation of agarose to generate aldehyde functions which are subsequently reacted at pH 4 to 6 with amines of the inhibitor to form Schiff bases which are then reduced with sodium borohydride or sodium cyano borohydride;
(d) the agarose may be converted into the hydraziosuccinyl derivative, to which carboxylic ligands may be attached with EDC or amines by diazotisation;
(e) cellulose fibers or beads may be converted into a hydrazide derivative and used according to the method of Parikh et al., Methods in Enzymology, Vol. 34, pages 77 to 102, editors W. B. Jakobi and Wilcheck, (Academic Press: NY);
(f) polyacryl amide beads may be coupled by direct glutaraldehyde procedure or by diazotisation of the the p-aminobenzamido ethyl derivatives or of the hydrazido derivative; and (g) finally, reference is made to glass beads (or other solid bodies) which can be coated with a protein, e.g., gelatin, which may be cross-linked and coupled to the inhibitor by methods analogous to any of the coupling methods described in German patent application P 3224837.7, Japanese patent application No. 116086/1982, United Kingdom Pat. No. 2103791 and U.S. Pat. No. 4,478,946.

The foregoing methods are known as such to persons skilled in the art and/or are described in the cited literature and require no detailed description.

The scope of the invention includes a process for making an affinity reagent which comprises covalently bonding to a carrier a Kunitz-type inhibitor of the type defined above, e.g., by any of the procedures set out above.

The scope of the invention further extends to all uses of the newly discovered tPA-inhibiting properties of the type of inhibitor which occurs in the aforesaid fraction code-named DE-3. This type of inhibitor will be referred to in the following as EtI (an acronym for "Erythrina-derived tPA inhibitor"), regardless of the source from which the inhibitor is derived in any particular case.

The affinity reagent according to the invention may be used for the manufacture of tPA and/or pro-tPA and of preparations comprising tPA and/or pro-tPA, e.g., in the process as set out above. However, the affinity reagent can also have utility as a diagnostic or analytical reagent.

The scope of the invention extends to pharmaceutical compositions comprising tPA prepared or purified by a process according to the present invention and/or pro-tPA dissolved in a physiologically compatible injection medium. Particularly preferred compositions comprise pro-tPA in mixture with tPA or comprise pro-tPA as the main active ingredient. More particularly, the composition is intended for the management of thrombosis or other conditions where it is desirable to produce local fibrinolytic or proteolytic activity via the mechanism of plasminogen activation.

DETAILED DESCRIPTION OF THE INVENTION

The invention will now be described by way of example, more particularly by way of the following non-limiting embodiment(s).

EXAMPLE 1

Preparation of affinity reagent according to the invention DE-3 inhibitor (EtI) is prepared as follows:

Erythrina latissima seeds are collected and processed according to the method of Joubert et al. The seeds are ground, defatted and extracted at 10° C. overnight with 0.5 molar sodium chloride solution. The extract is centrifuged and DE-3 inhibitor is recovered from the supernatant by ammonium sulphate precipitation followed by chromatography on Sephadex G50, DEA-cellulose and DEA-sepharose. The finally purified material migrates as a single band with an apparent molecular weight of 22,000 daltons when subjected to electrophoresis on a 15% polyacryl amide gel containing 0.1% sodium dodecyl sulphate (SDS).

Purified DE-3 (26 mg) is coupled to 5 ml of commercially available cyanogen bromide activated agarose in the usual manner (Sepharose 4b marketed by Pharmacia and who also supply the instructions for the use of the preparation). The affinity reagent is equilibrated against phosphate buffered saline of pH 7.4 containing 0.4M sodium chloride, 0.1% Triton X-100 (a commercial detergent commonly used in this art) and 0.02% sodium azideas a stabilizer. This affinity reagent is then packed into a 5 ml column fashioned from the barrel of a disposable plastics syringe.

EXAMPLE 2

Preparation and purification of tPA and pro-tPA

A medium containing tPA and pro-tPA is produced as follows: Human melanoma cell of a cell line known as Bowes cells RPMI-7272 (obtained from Denver Hospital, Denver, Colorado, and described in J. Biol. Chem. 256, 7035–7041) are grown as adherent monolayers in RPMI 1640 tissue culture medium supplemented with 10% heat inactivated (56° C.; 30 minutes) foetal bovine serum (FCS) and antibiotics (300 µg per ml penicillin; 200 µg per ml streptomycin and 10 µg per ml of tylocine). The cells are passaged at confluence (approximately $4 \times 10^5$ cells per cm$^2$) by trypsinisation and reseeding at $5 \times 10^5$ cells per 100 mm dish. After aspirating the medium, the cells are incubated in 0.25% trypsin in tris dulbecco's saline (24.8 mM tris HCl pH 7.4 containing 0.1 mM Na$_2$HPO$_4$, 5 mM KCl, 0.14M NaCl) at 37° C. for 5 minutes. Detached cells are dispersed by gentle pipetting and the suspension is added to an equal volume of medium containing foetal bovine serum to neutralize the protease. The cells are then washed by centrifugation at 350 g for 5 minutes, resuspended and reseeded into fresh dishes.

From these stock cultures the cells are grown as adherent monolayers in 75 cm$^2$ or 150 cm$^2$ tissue culture flasks and allowed to grow to near confluency in mediums supplemented with 10% foetal bovine serum. The cultures are then washed once and covered with 20 ml of serum-free medium. After 24 hours the medium is collected and fresh medium is added.

The harvest fluids are centrifuged at 2000 rpm for 5 minutes to remove whole cells and cellular debris. The solution is stabilized with Triton X100 (0,1%) or Tween 80 (0,1%) an acidified with glacial acetic acid (pH 5.5 to 6.0) for storage at −20° C.

2 l of harvest fluid are made 0.4 molar with respect to NaCl and are filtered through a 0.45 µm membrane. The filter harvest fluid is then applied to the affinity column at a flow rate of 45 ml/hour at room temperature. The effluent is collected at 4° C. and monitored for the presence of plasminogen-dependent fibrinolytic activity. No tPA or pro-tPA is detected.

After the total volume of harvest fluid has passed through, the column is washed with 6 column volumes of phosphate buffered saline containing 0.4M NaCl and 0.1% Triton X-100. No tPA or pro-tPA is eluted by this procedure.

Adsorbed proteins are then eluted using PBS containing 1.6M potassium thiocyanate, 0.4M NaCl and 0.1% Triton X-100.

The protein content is monitored by reading the absorbency at 280 nm. All plasminogen-dependent fibrinolytic activity is found to be eluted as a sharp peak when potassium thiocyanate is added to the eluting buffer, and this peak corresponds to a small protein peak.

The fractions containing the highest activity are pooled to give 6 to 8 ml solution stored at −20° C. and which represents 70 to 80% of the activity applied to the column. Fractions containing low activity are pooled separately. The total recovery of activity in both pools usually amounts to 90 to 100%. The potassium thiocyanate eluate contains a single band of protein with a molecular weight of 72 000 daltons corresponding to a mixture of pure tPA and pro-tPA, the latter in different runs amounting to from 39 to about 50% of the total or more.

The yields improve if the same column is used repeatedly over and over again. The column thus not only remains effective to be re-used many times, but in fact improves with use. This is surprising because tPA has the property of cleaving the inhibitor DE-3 when in its non-immobilized form.

EXAMPLE 3

Pharmaceutical preparation containing tPA and/or pro-tPA

The pooled fraction containing tPA and/or pro-tPA are dialyzed against 0.30 molar sodium chloride containing 0.01 volume percent Tween 80. Prior to administration the, concentration is adjusted to 75 µg per ml of tPa plus pro-tPA (for therapeutic purposes, the dosage rate for tPA is the same as for pro-tPA) and 0.3 molar NaCl. The solution is sterilized by filtration through an 0.22 µm membrane filter.

The tPA solution is administered intravenously by infusion at a dosage of about 80 mg per single treatment. In the case of pro-tPA, higher doses are required, for example, about 150 mg per single treatment.

EXAMPLE 4

Mass cultivation of melanoma cells

A spinner flask with Rosswell Park Memorial Institute culture medium 1640/10% foetal bovine serum is inoculated with melanoma cells at a concentration of $5 \times 10^5$ cells per ml. The flask is kept at 37° C. and stirred magnetically at 30 rpm. Medium is pumped out of the flask at a rate of 1% volume of the flask per hour and replaced at the same rate with fresh medium which has been equillibrated with 5% CO$_2$ in air. The cells are retained in the culture vessel by an outlet glass tube plugged with glass wool. The withdrawn medium is filtered through a millipore filter. The collected liquid is pasteurized.

EXAMPLE 5

Cultivation of Melanoma cells for high pro-tPA yields

Example 2 is modified by the addition to the culture medium of sufficient soybean trypsin inhibitor or alpha-1-anti-plasmin to inhibit the serum plasmin. In all other respects the process is carried out as in Example 2, the ratio of pro-tPA to tPA in the final product being now increased to approximately 9:1.

EXAMPLE 6

Elimination of residual tPA in mixtures of pro-tPA and tPA

The solution of tPA and pro-tPA is rendered 10 mM with respect to diisopropyl phosphofluoridate. The pH is adjusted to 8. After 4 hours the tPA has been permanently inhibited. The residual inhibitor is thereafter removed by dialysis.

EXAMPLE 7

Conversion of pro-tPA into tPA

An aqueous solution containing 100 µg of protein/per ml is mixed with an equal volume of phosphate buffered saline containing 5 μg/per ml of plasmin and is incubated for 16 hours at 20° C. Sodium dodecyl sulphate is added to a final concentration of 0.1% and the proteins are precipitated with 6% trichloracetic acid. The precipitate is washed in acetone and redissolved in 0,06M Tris HCl pH 6,8 containing 1% sodium dodecyl sulphate and 10% glycerol.

After this treatment it can be shown by electrophoresis that the pro-tPA has been converted completely into the active tPA form.

EXAMPLE 8:

Purification of tPA and pro-tPA

The recovery and purification procedures described in Example 2 were tested and found suitable for being applied to tPA and pro-tPA from the various genetically engineered sources described above. A single step will in some cases achieve adequate purification. Otherwise the remaining relatively minor contamination carried over from the culture medium is usually removable by relatively simple conventional techniques. For example, this applies in the case of cultures grown in the presence of serum. In those cases serum components are removed by subsequent final purification.

EXAMPLE 9:

Assay for E-inhibitor activity

The inhibitory activity of the EtI is expressed in terms of inhibitor units which are defined experimentally as follows:

(i) A sample of pure tPA is assayed fluorometrically by the method of Zimmerman et al (Proc.Natl.Acad.Sci. USA 1978, 75, 750) and adjusted to contain 50 fluorometric units of enzyme/ml of 0.1M Tris-HCl containing 0.02% Triton X-100.

(ii) The EtI sample is dissolved in 0.1M Tris-HCl pH 8.1 at a convenient concentration (usually 1-20 mg/ml, depending upon the expected specific activity of the inhibitor).

(iii) Serial two-fold dilutions of the inhibitor solution are prepared in 0.1M Tris-HCl pH 8.1 to a final dilution of 1/2048.

(iv) Each inhibitor dilution (10 μl volume) is mixed with 90 μl of the tPA solution and the tubes are incubated for 30 minutes at room temperature.

(v) Each tube is then assayed for residual enzyme activity and the logit transform of fractional residual activity is plotted as a function of the logarithm of the inhibitor dilution. The least squares regression line is fitted to these points and used to obtain the coordinates for "50% inhibition" by interpolation.

(vi) One unit of inhibitory activity is defined as that amount that will inhibit 1 fluorometric unit of tPA by 50%.

The standard assay employed is performed by adding enzyme to initiate the reaction in the following mixture.

|  | ml |
| --- | --- |
| Tris-HCl 0.1 M, pH 8.1 | 0.43 |
| Substrate 25 mM in DMSO | 0.01 |
| DMSO | 0.01 |
| Enzyme solution | 0.05 |
| TOTAL | 0.50 ml |

The mixture is vortexed briefly and placed in the sample chamber of a spectrofluorophotometer equipped with a recorder. Release of AMC is monitored at an activating wave-length of 383 nm and an emitting wave-length of 455 nm.

The instrument is standardized with pure AMC so that a full-scale recorder deflection is given by the above assay mixture in which 10 μl of $2 \times 10^{-5}$M AMC in DMSO replaces the 10 μl of DMSO (i.e., a full-scale recorder deflection is given by 200 pmoles of AMC or by 0.5 ml of a $4 \times 10^{-7}$M solution of AMC in the assay mixture).

One fluorometric unit of the enzyme activity is defined as that amount that will catalyze the release of 10 p moles of AMC/min at 20° C.

The following is a specific example of such determination:

A partly purified fraction containing EtI freeze-dried at 5 mg/vial and reconstituted at 2.5 mg/ml.

Doubling dilutions performed in 0,1M Tris HCl pH 8.1.

Standard t-PA solution 47.3 μ/ml

10 μl inhibitor dilution + 90 μl t-PA; 30 min at room temperature; assay enzyme activity in mixture.

Results

| Sample | Inhibitor dilution | Enzyme activity (FU/ml) | Residual activity (R) (%) | $\text{Logit} = \log\left(\frac{R}{100-R}\right)$ |
| --- | --- | --- | --- | --- |
| 1 | No inhibitor | 42.6 | 100 | — |
| 2 | 1/16 | 2.22 | 5.2 | −1.261 |
| 3 | 1/32 | 3.98 | 9.34 | −0.857 |
| 4 | 1/64 | 6.69 | 15.70 | −0.730 |
| 5 | 1/128 | 11.08 | 26.00 | −0.454 |
| 6 | 1/256 | 16.64 | 39.05 | −0.193 |
| 7 | 1/512 | 23.00 | 54.00 | 0.397 |
| 9 | 1/2048 | 34.08 | 80.00 | 0.602 |

Regression equation:

$$\text{Logit } R = 0.885 \log (1/\text{dil}) - 2.3232$$

where R = residual activity and logit R = log R/(100-R)
50% inhibitory dilution = 1/423
10 μl of a 1/423 dilution of 2.5 mg/ml inhibitor solution inhibited 50% of 4.26 units.
Specific activity is therefore 4.26 units × 1/0.01 ml × 423 × 1/2.5 mg = 72 100 units mg.

EXAMPLE 10

The procedure essentially as described in Example 1 was applied to samples of seeds of a considerable number of Erythrina species to produce chromatographic fractions which were screened for tPA-inhibitor activity using the method described in Example 9. Without exception, each sample yielded a fraction exhibiting the desired activity to a greater or lesser extent, depending on the degree of purification and concentration achieved with the particular fraction.

It is to be emphasised that in the case of *E. latissima*, the desired activity happened to occur in the third chromatographic peak, obtained by chromatography on a DEAE - agarose column following a number of previous concentration and purification steps. However, this was not necessarily the case with all remaining species. In some cases, the activity was eluted in the first peak which emerged from the column. In others, as many as six peaks preceded the desired active peak. However, the active fractions are readily identifiable by standard tests adapted to the determination of tPA-inhibition as given below.

Seeds from nine species of Erythrina seed were tested and showed inhibiting activity as reported below:

| Species | Activity (Iu/mg) |
|---|---|
| E. latissima | 40,000 |
| E. caffra | 50,000 |
| E. lysistemon | 27,200 |
| E. zeyheri | 15,800 |
| E. decora | 20,800 |
| E. humeana | 20,500 |
| E. abyssinica | 5,000 |

I claim:

1. A process for selectively and reversibly adsorbing tPA (tissue plasminogen activator), pro-tPA or mixtures of both, from an aqueous medium containing such substance or substances in solution which comprises intimately contacting said aqueous medium with an affinity reagent comprising an immobilized Kunitz type inhibitor, derivable from an Erythrina species, and having the following combination of characteristics:
   (a) it is an inhibitor of the Kunitz type;
   (b) it inhibits trypsin;
   (c) it inhibits plasmin;
   (d) it has no effect on urokinase;
   (e) it inhibits tPA; and
   (f) in its immobilized form, it is a selective adsorbent for tPA and its precursor pro-tPA,
to cause the tPA, pro-tPA or mixture of both to become selectively adsorbed on the affinity reagent.

2. A process applied to the purification of tPA, pro-tPA or mixtures of both which comprises intimately contacting an aqueous medium containing dissolved tPA, pro-tPA or a mixture of both with an affinity reagent comprising an immobilized Kunitz type inhibitor derivable from an Erythrina species, and having the following combination of characteristics:
   (a) it is an inhibitor of the Kunitz type;
   (b) it inhibits trypsin;
   (c) it inhibits plasmin;
   (d) it has no effect on urokinase;
   (e) it inhibits tPA; and
   (f) in its immobilized form, it is a selective adsorbent for tPA and its precursor pro-tPA,
thereby selective adsorbing the tPA, pro-tPA or mixture of both from the medium; separating the affinity reagent loaded with tPA, pro-tPA or mixture of both from contact with said aqueous medium and non-adsorbed materials; and desorbing the tPA, pro-tPA or mixture of both from the affinity reagent and collecting the desorbed tPA, pro-tPA or mixture of both.

3. A process according to claim 2, wherein the tPA or pro-tPA or mixture is contaminated with urokinase and the urokinase is removed with the non-adsorbed material.

4. A process according to claim 2, wherein said aqueous medium is obtained from cultivating a melanoma cell culture.

5. A process according to claim 2, wherein the pro-tPA is enzymatically converted into tPA before or after the adsorption step and out of contact with the affinity agent.

6. A process according to claim 2, wherein the tPA, pro-tPA or mixture of both is adsorbed by passing said aqueous medium containing it through a bed of the affinity reagent, followed by washing the bed and subsequent desorption of the tPA, pro-tPA or mixture of both off the bed.

7. A process according to claim 2, said desorbing comprising contacting the loaded affinity reagent with an aqueous potassium thiocyanate solution.

8. A process according to claim 2 for purifying pro-tPA in which said aqueous medium is produced by cultivating a pro-tPA yielding cell culture in a suitable culture medium in the absence of enzymes which catalyze the conversion of pro-tPA into tPA or, if such catalytic enzymes are present, in the presence of a suitable inhibitor which inhibits the catalytic activity of such enzymes.

9. A process according to claim 2, wherein said aqueous medium is produced by cultivating pro-tPA yielding melanoma cells in a serum-containing culture medium in the presence of an inhibiting amount of one or more inhibitors which inhibit serum enzymes which catalyze the conversion of pro-tPA into tPA.

10. A process according to claim 1, wherein said aqueous medium also contains urokinase and which comprises intimately contacting said urokinase-containing aqueous medium with said affinity reagent to selectively adsorb the tPA, pro-tPA or mixture of both, from the solution, withdrawing the affinity reagent loaded with tPA, pro-tPA or mixture of both from contact with resultant aqueous medium depleted of tPA, pro-tPA or mixture of both, but still containing urokinase, and separating the urokinase from said resultant aqueous medium.

11. A process according to claim 10, wherein the adsorbed tPA or pro-tPA or mixture of both is desorbed and collected.

12. A process according to claim 10, wherein said separating of said urokinase is conducted by adsorbing said urokinase from the aqueous medium using an affinity reagent having an affinity for urokinase.

13. A process according to claim 1, wherein said Erythrina species is *Erythrina latissima*.

14. A process according to claim 2, wherein said Erythrina species is *Erythrina latissima*.

* * * * *